United States Patent
Wechsler et al.

(10) Patent No.: US 6,844,187 B1
(45) Date of Patent: Jan. 18, 2005

(54) BIOREACTOR

(75) Inventors: Thomas Wechsler, Zurich (CH); Ulrich Baer, Heiden (CH); Christian Oehr, Herrenberg (DE); Thomas Graeve, Stuttgart (DE)

(73) Assignee: Sefar AG, Rueschlikon (CH)

( * ) Notice: Subject to any disclaimer, the term of this patent is extended or adjusted under 35 U.S.C. 154(b) by 72 days.

(21) Appl. No.: 10/030,697

(22) PCT Filed: Jul. 5, 2000

(86) PCT No.: PCT/EP00/06355
§ 371 (c)(1),
(2), (4) Date: Apr. 10, 2002

(87) PCT Pub. No.: WO01/04262
PCT Pub. Date: Jan. 18, 2001

(30) Foreign Application Priority Data

Jul. 12, 2000 (DE) .......................... 199 32 439

(51) Int. Cl.⁷ .............................................. C12M 3/06
(52) U.S. Cl. ............................. 435/297.2; 435/299.1; 435/395; 435/402
(58) Field of Search ................................. 435/395, 398, 435/399, 401, 402, 293.1, 297.2, 297.4, 297.1, 299.1; 210/321.84

(56) References Cited

U.S. PATENT DOCUMENTS

| | | | | |
|---|---|---|---|---|
| 4,201,845 A | * | 5/1980 | Feder et al. ............ | 435/297.2 |
| 4,225,671 A | * | 9/1980 | Puchinger et al. ......... | 435/70.3 |
| 4,734,372 A | * | 3/1988 | Rotman ....................... | 435/29 |
| 4,833,083 A | | 5/1989 | Saxena | |
| 5,190,878 A | * | 3/1993 | Wilhelm .................. | 435/297.2 |
| 5,688,687 A | * | 11/1997 | Palsson et al. ........... | 435/293.2 |
| 6,218,182 B1 | * | 4/2001 | Naughton et al. .......... | 435/395 |
| 6,228,607 B1 | * | 5/2001 | Kersten et al. ............... | 435/41 |

FOREIGN PATENT DOCUMENTS

| | | | |
|---|---|---|---|
| EP | 0 113 328 | 7/1984 | |
| EP | 155237 A2 | * 9/1985 | ............ C12M/3/02 |
| EP | 0 909 811 | 4/1999 | |
| JP | 57166985 A | * 10/1982 | ............ C12P/1/00 |

\* cited by examiner

Primary Examiner—William H. Beisner
(74) Attorney, Agent, or Firm—Oblon, Spivak, McClelland, Maier & Neustadt, P.C.

(57) ABSTRACT

The invention relates to a bioreactor as well as a method for cultivating organic material: in particular cells, by means of a nutrient medium. For an intensive cultivation of the organic material in a simple and reliable handling a flow generating device is provided in the bioreactor according to the invention, by means of which the nutrient medium can be put into a flow, wherein a receiving device is arranged in the flow that is adapted for receiving and/or retaining the organic material and wherein the receiving device that is adapted for passing through the flowing nutrient medium is permeable. The method in accordance with the invention is characterized in that the nutrient medium is at least temporarily put into a flow, that the organic material, in particular cells, is retained in or at a receiving device, which is permeable to the nutrient medium and that the nutrient medium is passed through the receiving device.

16 Claims, 6 Drawing Sheets

BIOREACTOR

The invention relates to a bioreactor as well as a method for cultivating organic material as described herein.

The cultivation of organic material, in particular of human or animal cells, increasingly gains in importance in medical diagnostics, therapy and pharmacology.

Of particular interest in this is the multiplication of hematopoietic parent cells. These are taken from a patient before a radiotherapy or chemotherapy and are to be retransplanted into the patient in a greatest number possible after the conclusion of the radiotherapy or chemotherapy.

In this method, among others, cryoconservation is commonly used, in which withdrawn blood parent cells are frozen for the duration of the radiotherapy or chemotherapy. However, an enrichment of the cells is not possible with this. On the contrary, the number of living cells and their vitality is drastically reduced.

Methods for cultivating and enriching different cells of human origin have already been developed and established.

Typically, cells are cultivated in containers or Petri dishes, in which a nutrient medium is located that is suitable for the cultivation of the respective cell type. In general, several treatment steps are required during the cultivation, such as the exchange of the nutrient medium as well as a displacement of cultivated cells into other containers.

Due to the repeatedly required interference in the cultivation process there is a growing risk of contaminating the cell material, for example through laboratory equipment or the ambient atmosphere, as a result of which the material to be cultivated becomes useless for the further utilization.

In all, the handling of the entire cultivation process entails relatively great expense so that a clinical utilization on a large scale is hardly practicable.

Furthermore, a cultivation of cells in hollow fibres was tested. Here the cells located in the hollow fibres are diffusively supplied with nutrients from the fibre periphery. At the beginning of the cell cultivation relatively good growth rates can be achieved with this, but with an increasing number of cells present in the spatially limited hollow fibres a further multiplication becomes problematic.

A similar problem exists in the bioreactor and the method according to EP 0 121 981 A1. A porous, mnolithic ceramic block, which is interspersed with a number of fine channels that extend in parallel, is inoculated with cells. The cells add to the porous inside of the channels, which are flowed through by a nutrient solution. Another bioreactor used for the diffusive supply of cells, which is designed in layers, is known from U.S. Pat. No. 5,605,835.

From the preamble-forming EP-A-0 909 811 a bioreactor and a method employing a convective supply of the organic material can be taken. In this known bioreactor a cylindrical construction with concentrically arranged partition walls is provided, between which the organic material is located in an annular receiving space. Depending on the type of organic material to be cultivated the receiving space needs to be adapted in size and shape.

A further bioreactor having a comparable cylindrical construction is known from U.S. Pat. No. 4,833,083.

In EP-A-0 113 328 a bioreactor with a cylindrical chamber is disclosed. The feeding and discharge of the nutrient medium is effected by means of a number of porous tubes, which project into the chamber.

The invention is based on the a object to develop a device and a method for cultivating organic material, which allow an intensive cultivation of an organic material on the one hand and can be handled in a particularly easy and reliable manner on the other hand.

The object is solved in accordance with the invention by the bioreactor and method of use as described herein.

The bioreactor is based on the convective supply of the bioreactor and method of use as described herein organic material with nutrient medium. This supply can take place in a continuous or quasi-continuous manner. By this it is possible to ensure an almost optimum provision of the required nutrients over the entire duration of the cultivation, while metabolic products, which are detrimental to cell growth, are at the same time quickly removed by the flow of the nutrient medium. Tests carried out with hematopoietic parent cells have shown excellent growth and vitality rates.

The bioreactor includes a closed housing having at least one feed and one discharge and at least a flow channel, and here a gradient or commonly used pump devices, such as hose pumps, can be employed to generate the flow.

In principle, other devices that are capable of putting the nutrient medium into flow are also suitable. The rate of flow and the quantity of flow are adjusted in such a way that the organic material remains largely immobilized in the receiving device. The nutrient medium flows transversely through the receiving device from one partition wall element to the other, with the organic material being arranged in a substantially transverse manner to the flow.

With the bioreactor according to the invention an uninterrupted supply of the organic material with the necessary nutrient media and substances is rendered possible through a feeding taking place during the entire cultivation process, as a result of which the handling and performance of the cultivation process is simplified to a considerable degree. Due to the omission of a repeated external interference in the cultivation process and of the greater risk of contamination related therewith the reactor according to the invention is also particularly suited for the large-scale clinical use.

The constantly good supply of the organic material with nutrients allows an intensive cultivation of the material, whereby enrichment values of the cells can reach the factor 10 and above. By comparison, in the cultivation of cells in cultivating containers or Petri dishes enrichment factors are typically achieved that merely range between 2 and 4 despite a considerably greater expense.

In general, the bioreactor in accordance with the invention is suited for cultivating various kinds of organic material. Concerned here are preferably simple structures, such as bacteria, viruses, fungi or body cells. Apart from the parent cells these are, among others, microvascular and macrovascular endothelial cells from the splee, the suprarenal gland and the aorta, different cell types from the cornea, cells of the eye lens and the retina, cells from the skin, bones as well as the bone marrow. In principle, the cultivation of more complex structures, for instance of entire organs or parts thereof, is also possible.

The bioreactor in accordance with the invention is characterized in that the receiving device has at least two partition wall elements, by which a receiving space is enclosed, that the organic material is arranged in the receiving space and that the partition wall elements are on the one hand permeable to the nutrient medium and on the other hand substantially impermeable to the organic material. Due to the impermeability of the partition wall elements to the organic material a defined immobilization of the organic material in the receiving device is achieved on the one hand. A washing away of the organic material is prevented, as this is enclosed in a defined space in the flow. In this defined space, which preferably extends over the entire flow cross section and has a relatively small design, the organic material can also move to a certain extent, which leads to a uniformly good settlement with cells. On the other hand, owing to the permeability of the partition wall elements to the nutrient medium a continued good convective supply of the organic material and consequently an intensive cultivation of the same is ensured.

In principle, different kinds of material are possible for being used in the partition wall elements, which have the required permeability for a medium to be fed. They can consist e.g. of fabrics, wafts or felts or of other permeable materials. Fabrics have proved to be particularly useful for bioreactors employed for cultivating liver cells. With their relatively coarse meshes fabrics generate an excellent diffusion effect in the flowing nutrient medium.

It is intended that the partition wall elements have a membrane. Since membranes can be produced with differing properties regarding their permeability as well as their selective behaviour, the supply of the cells that are to be cultivated in the bioreactor with particular substances can be specifically influenced by using a suitable membrane. Moreover, by choosing membranes, which are reinforced in different manners, the mechanical stability of the partition wall elements can likewise be specifically adjusted and adapted to the respective requirements of the organic material, e.g. in the case of adherent cells. As reinforcement of the membrane for instance textile reinforcements, such as fabrics or wefts, can be used. The use of organic or anorganic membranes, for example of a polymer, metal or ceramics or of a combination of these materials, is possible.

In order to obtain a particularly good immobilization of the organic material provision is made in the bioreactor according to the invention for the receiving device to include a carrier element, which is adapted for adding the organic material and is permeable to the nutrient medium. An addition of the organic material to the substantially plane carrier element can be achieved by a specific structure of the carrier element and/or by the flow pressure, The carrier element can constitute the receiving device in combination with the partition wall elements. This embodiment is suited, among others, for the cultivation of implants, for instance of in-vitro cultivated skin areas, for which a large-surface arrangement of the immobilized cells is required.

In this it is of advantage if the carrier element includes a textile carrier material. Through the appropriate choice e.g. of the fabric type and material, the filament strength, the mesh width and the number of threads an almost ideal relation between surface and reactor volume as well as good flow properties for the nutrient supply of the cells can be adjusted in a simple way for each case of application. This allows a specific influencing and promotion of the cultivation of the organic material.

As textile carrier materials technical fabrics, wefts and folds are suitable, in which the structure of monofilaments or wires is exactly defined. The monofilaments or wires may consist for example of metal, ceramics, synthetic and/or natural materials, such as cellulose, with or without surface coatings. In particular cases multifilament fabrics are also useful, in which the threads that define the fabric structure consist for their part of a number of smaller threads.

A specific incorporation of cells in the carrier element can be achieved by a three-dimensional structure. The carrier element can be for instance a so-called three-dimensional technical fabric. Fabrics of this type have two or more superposed and partly connected or woven fabric matrices that offer a secure support for incorporated cell material. Furthermore, a three-dimensional structure can be obtained by folding, pleating or rolling an approximately two-dimensional element. In addition, a skeleton structure of the carrier element or an arrangement of structural elements, as for example tube members or honeycombs, can be provided. Finally, so-called non-woven materials and bonded fabrics can also be applied.

When using technical fabrics as carrier element it is of advantage if the technical fabric in surface-treated and a bio-compatible surface with a structure adapted for an adhesion of the organic material is formed. In this way the surface of a stable fabric, for example of polyester, polyamide, a trifluorehtylene/ethylene copolymer, metal or ceramics, can be specifically functionalized for different purposes. For instance cell growth can be positively influenced by generating a hydrophilic fabric surface or by increasing the concentration of nitrogenous functional groups. By comparison, other substances, such as e.g. immunoglobulin G (IgG), are preferably adsorbed at hydrophobic surfaces.

A particularly effective surface treatment are low temperature plasma methods, by means of which for example textile materials of polymer, metal or ceramics and membranes can be specifically coated with an inert surface and thus be functionalized without having to expose the fabric to be treated to aggressive solutions or high temperatures. In this way different material properties, such as e.g. a high mechanical stability of a basic carrier material, can be systematically combined with desired surface properties, such as e.g. hydrophilicity and cell adhesion.

It is intended that the receiving device preferably has a circular design. In a circularly designed hollow space in the flat cell a particularly good flow and consequently a constant supply of the cells to be cultivated with nutrient medium is ensured. The flat cell can be designed in layers, for instance of glued plastic elements, which results in a bioreactor that is compact and at the same time simple to produce. The simple producibility even allows the employment of the bioreactor as a single-use article, which may be of advantage for medical applications. At the same time the flat cell is of such robustness that a saterilisation carried out by means of autoclaving or γ-sterilisation is possible. For the inoculation and reaping of larger organic material, as for example of implants, the bioreactor can be mounted or dismounted.

In another embodiment of the invention it is of advantage if a number of flat cells are arranged as modules in one flow direction in a parallel and/or serial fashion. In this the medium flowing from a first flat cell can be directly fed to further flat cells such that a particularly effective use of the nutrient medium and a possible utilization of metabolic products of a previous cell is rendered possible. As a rule, however, a parallel arrangement is useful in order to exclude any contamination caused by metabolic products.

In a preferred embodiment of the bioreactor a control device is provided, by means of which the flow generating device, a temperature adjusting unit, a gaging unit and/or further supply units can be controlled and/or regulated. Through this it is possible to specifically influence the cultivation process of the organic material through various parameters, such as the rate of flow, the quantity of flow, the temperature and pressure of the nutrient medium as well as the feeding and discharge of further media and substances.

In particular, a control or a regulation of, the different units by the control device is possible through a central predetermination of specific control or regulation programmes, which are brought into line with individual organic materials or cultivation processes according to requirement. Thus, an adjustment and control of different process parameters that is tailored to suit the requirements is rendered possible.

In this it is particularly advantageous if a sensor device is arranged in one flow direction after the receiving device, by means of which physical and chemical values of state of the nutrient medium can be determined and the sensor device is connected to the control device. With the sensor device e.g. the concentration of the nutrients or metabolic products present in the nutrient medium can be determined. Finally, due to the coupling of the sensor device to the control device a possibly required change of the chemical and physical values of state of the nutrient medium can be carried out. On account of the described coupling this change can be effected almost in "real time", i.e. in a direct succession to the determination of the corresponding values of state.

Finally, in a preferred embodiment the bioreactor is characterized in that a closed housing is provided, in which the receiving device is arranged and at least one feed and one discharge are provided for the nutrient medium as well as an access for introducing and removing the organic material. Through the closed housing it is ensured that the inside, especially the receiving device of the bioreactor, still remains sterile after the production and sterilization of the bioreactor even after storage and transport. Moreover, a contamination-free cultivation of the organic material is rendered possible, since the individual treatment steps, e.g. the introduction and discharge of the organic material as well as the feeding and discharge of the nutrient medium or of other substances, can be performed with the housing being closed and thus the risk of a contamination of the organic material can be decreased considerably. Due to the simple construction of the bioreactor it can be produced at low cost and is particularly suited for being employed as a single-use article in the clinical field.

One aspect of the method in accordance with the invention resides in the fact that the nutrient medium, which is put into a flow, is passed through the receiving device retaining the organic material. Through this a cultivation of the organic material that is easy to handle and reliable is possible. In particular, by passing the nutrient medium through the receiving device, a good supply of the organic material retained thereon or therein with nutrients is ensured, as a continuous flowing round or, if required, infiltration with nutrient solution is achieved. The flow can be constant or pulsating.

In order to keep the risk of contamination for the organic material to be cultivated particularly small, it is of advantage if the receiving device is sterilized prior to inoculating or introducing the organic material into the former. The sterilization of the receiving device can be carried out e.g. on the part of the producer immediately after the production of the bioreactor. Through suitable measures taken to close the bioreactor the sterility of the receiving device can then be maintained until the time of application. However, it is also possible to carry out the sterilization of the receiving device only immediately before its application. In principle, both measures can be combined to ensure a particularly great freedom from contamination. Besides, a sterilization of the entire bioreactor is also possible, for example if especially high demands are made on securing sterility.

For a further simplification of the cultivation process it is intended that prior to the removal of the cultivated organic material a medium, in particular a physiological solution with an enzyme, such as a trypsine solution, is introduced for detaching and rinsing out the added organic material. Through this an interference in the closed bioreactor, as it is required for instance in the case of a mechanical detachment of the added organic material with suitable instruments, becomes unnecessary. Apart from this simplification of the handling the risk of both a contamination and a mechanical damage of the fabric can be greatly reduced as a result of this non-invasive detachment of the material. The rinsing solution can be fed through the same access as the inoculation with organic material. During the inoculation and the rinsing out, which is also referred to as reaping, it is useful to interrupt the nutrient medium flow.

A preferred embodiment of the method provides that the direction of flow of the nutrient medium, which is passed through the receiving device, is changed during the cultivation of the organic material. With this a good supply of the cells can be obtained especially in the case of organic material that has a great lateral extension and thickness. Any nutrient gradients that might appear in the material can be appreciably reduced in this way.

To ensure a supply of the organic material with nutrients, which is adapted to the respective duration of the cultivation process, and to achieve thereby an intensive cultivation of the organic material provision is made in the method according to the invention that the material composition, the stoichiometrical composition, the state or rate of flow of the nutrient medium are changed during the cultivation.

Moreover, it is of advantage in this if chemical and/or physical values of state of the nutrient medium are measured when the nutrient medium is passed through the receiving device, that the measured values of state are analysed and the chemical and/or physical values of state of the nutrient medium are changed depending on the measured values of state. In this way chemical and/or physical parameters of the nutrient medium or of additional nutrients can be adapted particularly well to the changing requirements of the cells in the course of the cultivation process. In addition, especially metabolic products of the organic material can be determined through a lactate or $CO_2$ value present in the nutrient medium and can be employed very well for the control, monitoring and documentation of the cultivation process. This way the best moment for reaping can be determined, for example immediately before an undesired differentiation taking place during the cultivation of parent cells.

In the following a detailed description of the invention will be given with reference to drawings of preferred embodiments. In an extremely schematized representation

Figure 1:
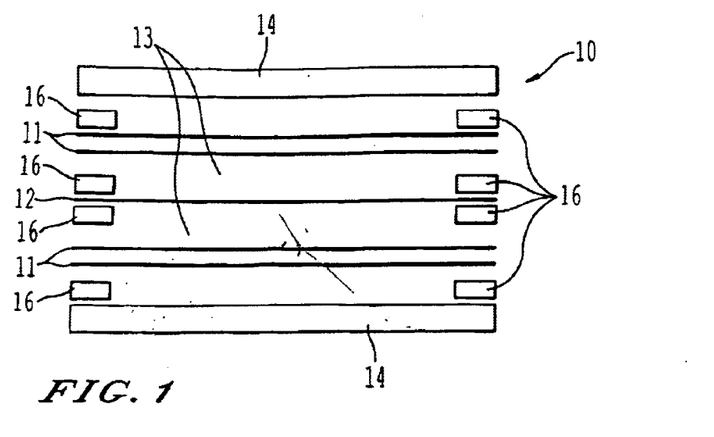
FIG. 1 shows a cross section of a preferred embodiment of the bioreactor according to the invention as flat cell.

The cross section shown in FIG. 1 of a preferred embodiment of a bioreactor 10 according to the invention for cultivating parent cells has a carrier element 12, partition wall elements 11, which are spaced therefrom and each consist of two parts, and a cover 14 located on both sides. Due to the distance pieces 16, which are provided between the individual elements and can be separate ring elements or part of the housing, an adjustment of a desired distance between the carrier element 12 and the partition wall element 11 or between the partition wall element 11 and the cover 14 is possible.

The covers 14 and the distance pieces 16 are produced of polycarbonate. The carrier element 12 is designed as a technical fabric. As fibre material preferably a monofilament consisting of polyamide 6.6 (PA 6.6) or polyethyleneterephtalate (PET) is used. The mesh width of the fabric amounts to an average of 20 $\mu$m and a thickness of approximately 55 to 60 $\mu$m. The weight of the fabric amounts to approximately 35 to 40 g/m$^2$.

A receiving device for the organic material is constituted by the carrier element 12 and the partition wall elements 11, which laterally define a receiving space 13 of the receiving device. In the illustrated example the partition wall elements 11 each have a membrane, which is applied to a supporting fabric lying underneath. The membrane material includes polyamide 66 (PA 66). As supporting fabric for example monofilament fabrics made of polyethyleneterephtalate (PET) can be employed having a mesh width of approximately 265 $\mu$m, a thickness of around 200 $\mu$m and a typical weight of 85 g/m$^2$. Typical membrane thicknesses range between 0.45 $\mu$m and 0.8 $\mu$m. For the spacing of the individual elements of the bioreactor the distance pieces 16 have a height of about 3 mm.

Figure 2:
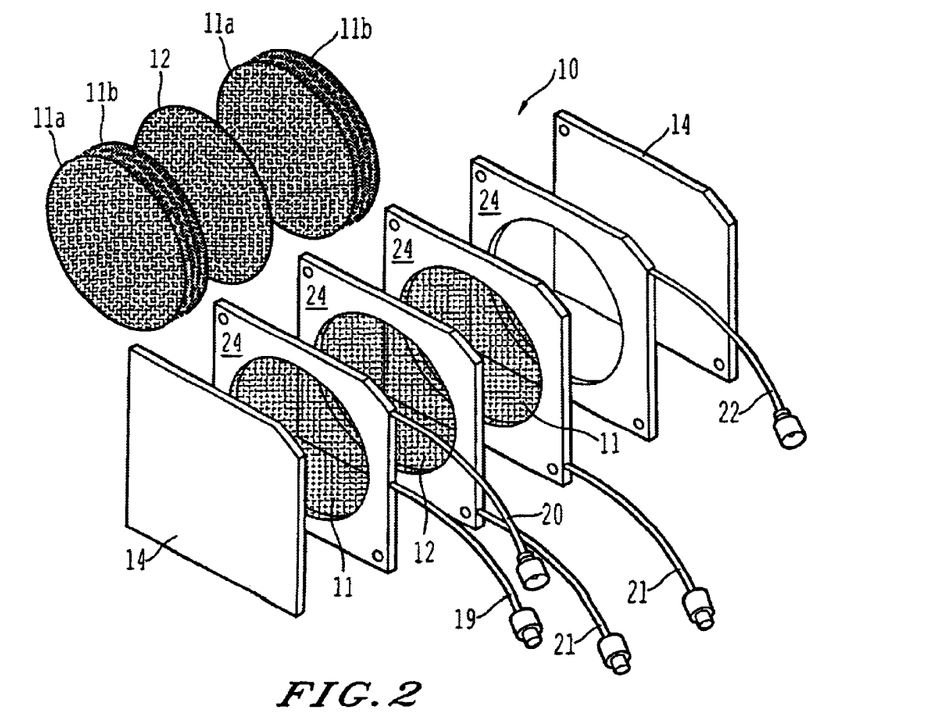
FIG. 2 shows a view onto an assembly of individual components of a bioreactor according to the invention.

FIG. 2 shows a view onto an assembly of individual components of the bioreactor 10 according to the invention. Between the two covers 14 there are several annular carrier plates 24, to which the carrier element 12 or the partition wall elements 11 are mounted that consist of a membrane 11$a$ and a supporting fabric 11$b$. The circular forms of the employed fabrics or membranes are cut to a precise fitting, for example by means of a laser, with the carrier element 12 that is designed as technical fabric and the partition wall elements 11 being attached to the carrier plates 24 by means of an adhesive that is hardenable under ultraviolet light or welded thereto, Together with the covers 14 the annular carrier plates 24 form a housing with a hollow space, into which lead lines for the feeding and/or discharge of fluids. In the present embodiment the feeding of the nutrient medium into the bioreactor 10 is effected via the feed line 19, while the discharge line 22 is provided for discharging the nutrient medium. The inoculation of the organic material as well as the feeding of a medium containing enzymes for detaching the added organic material is effected via two lines that lead into the receiving device of the bioreactor 10. For the ventilation of the bioreactor 10 a vent line 20 is arranged at the carrier plate 24 with the feed line 19.

As is shown in this embodiment, the carrier plates 24 that basically have the same construction take over the function of the distance pieces 16 depicted in FIG. 1. By variating the thickness of the individual carrier plates or of the distance pieces 16 the distance of the individual components of the bioreactor 10 can be excellently adapted to the conditions required for the cultivation of specific organic materials, An important role in this plays the relation of the reactor surface to the reactor volume, which can be adjusted by choosing the appropriate fabrics. Moreover, the distance between the individual components can also be slightly changed for example by inserting different sealings or intermediate plates, and here a dismounting is also possible by means of detachable mounting means. Furthermore, the covers 14 can be followed by temperature cabinets (not depicted), which serve to maintain a constant process temperature during the cultivation of the organic material. Such temperature cabinets typically have an electric heating and/or cooling or are connected to a heating or cooling bath via feed and discharge lines. In principle, the storage of the bioreactor in a tempered warming cupboard is also possible.

Figure 3:
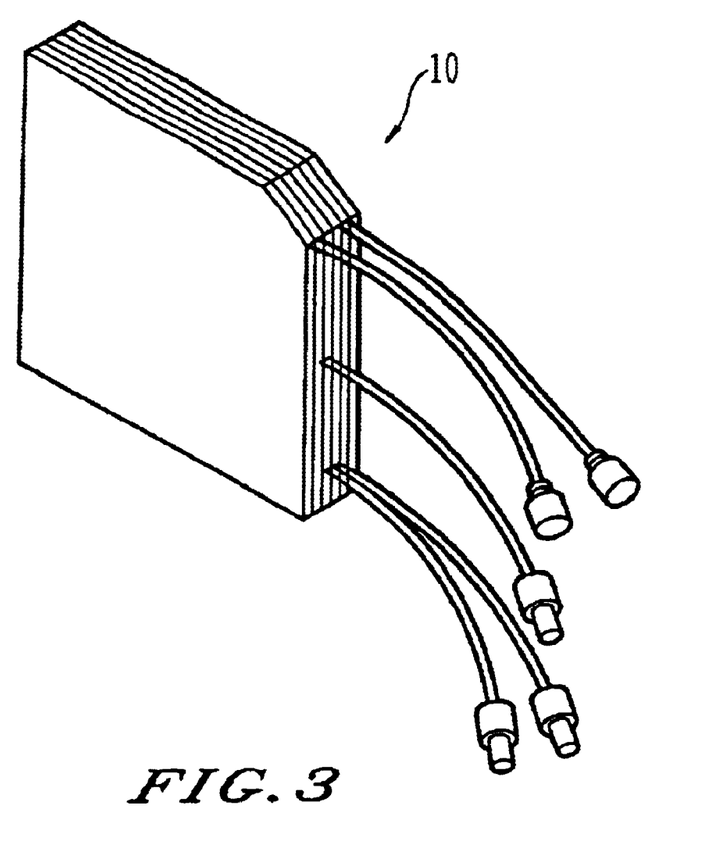
FIG. 3 shows an assembled bioreactor as flat cell.

The bioreactor 10 described in FIG. 2 with its individual components is shown in FIG. 3 as assembled, finished flat cell with feed and discharge lines. The bioreactor 10 in accordance with the invention has a compact format, which particularly simplifies its handling in the laboratory field as well as in the clinical field, In connection with the diagram according to FIG. 4 a brief description is given of the most important steps in the operation of the bioreactor 10 that is employed for the cultivation of peripheral, hematopoietic parent cells. These parent cells are required for the transplantation of blood parent cells after a high dosage chemotherapy.

Figure 4:
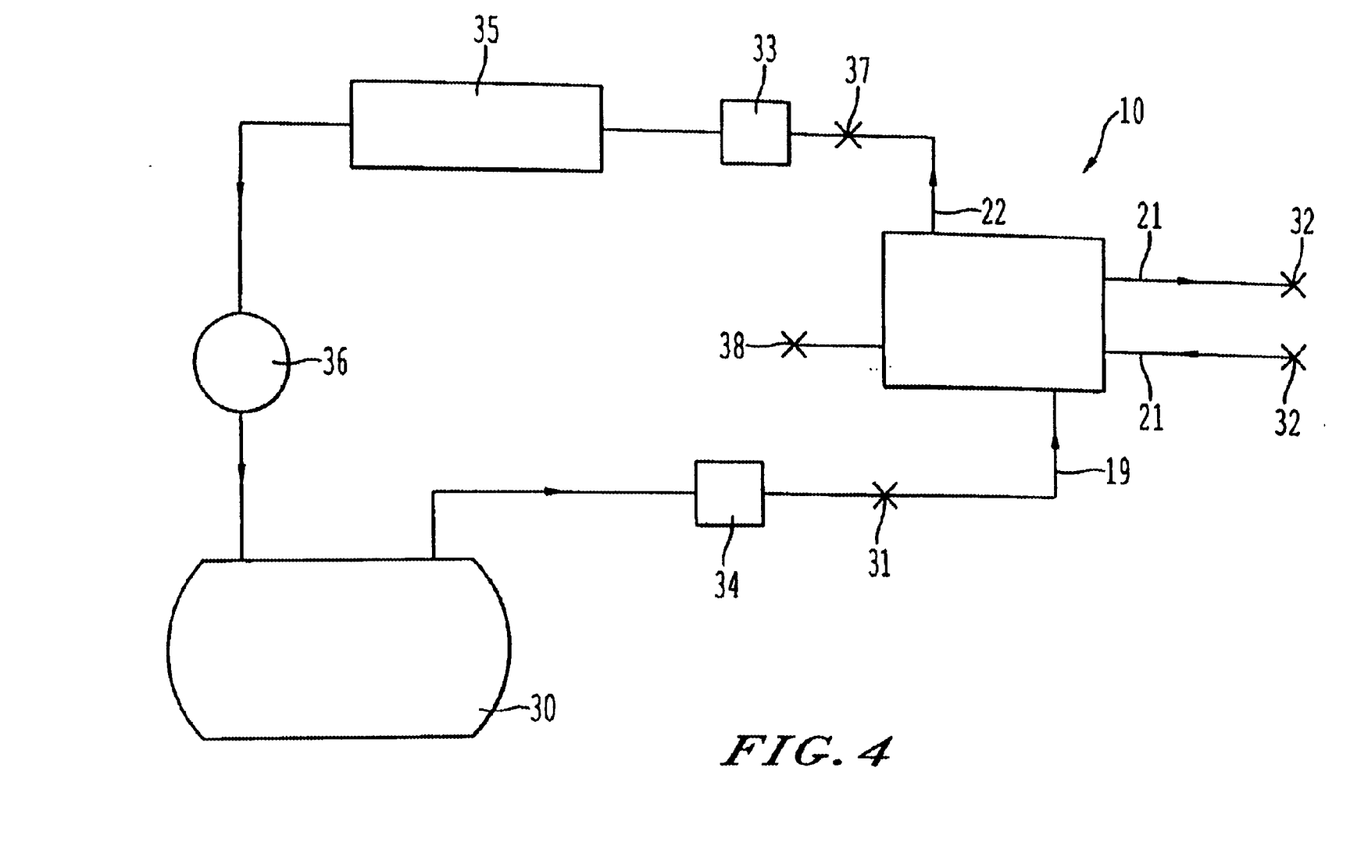
FIG. 4 shows a diagram of an installation with a bioreactor.
Figure 5:
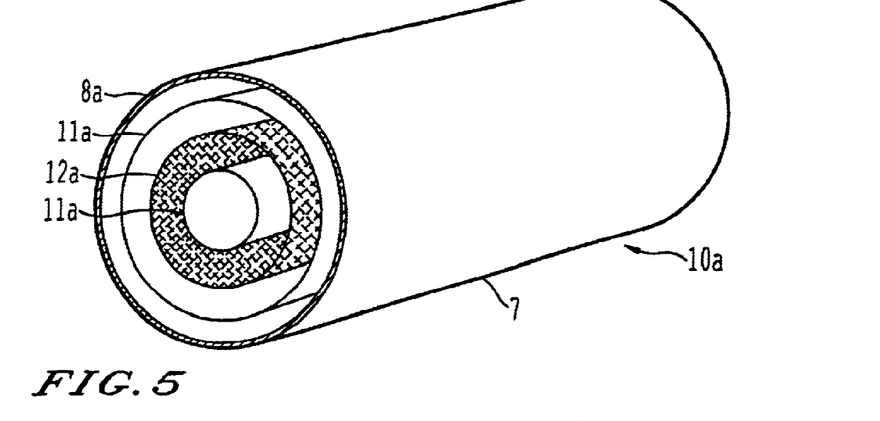
FIG. 5 shows a schematic view of the bioreactor according to another embodiment of the invention.
Figure 6:
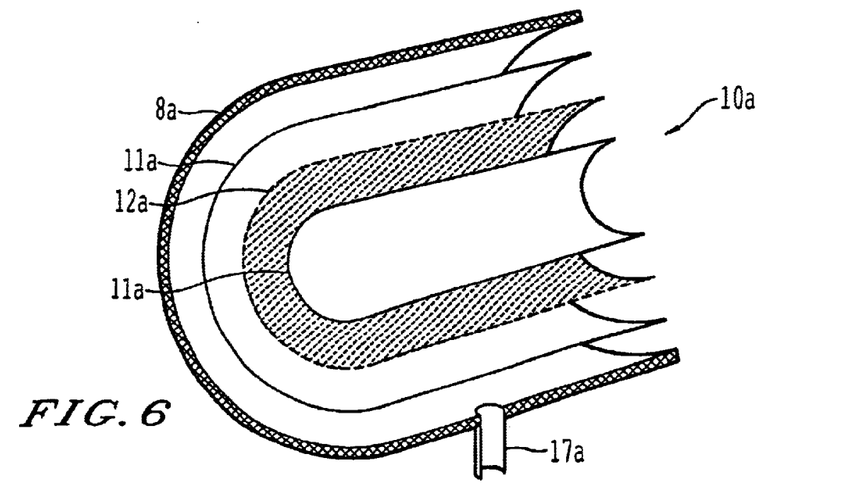
FIG. 6 shows a schematic cross-sectional view of the bioreactor of FIG. 5.
Figure 7:
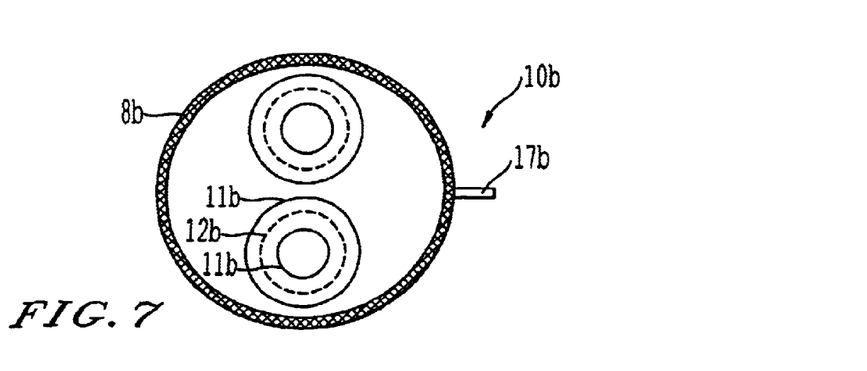
FIG. 7 shows a cross-sectional view of the bioreactor according to another embodiment of the invention.
Figure 8:
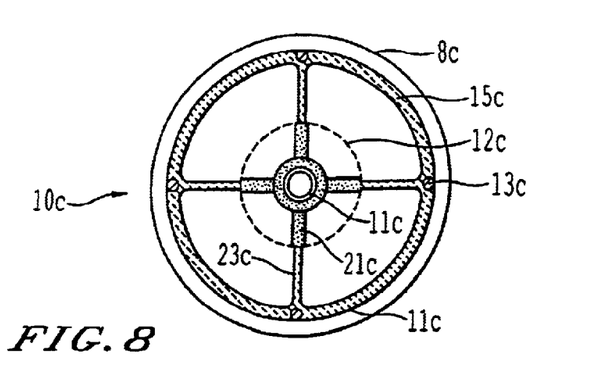
FIG. 8 shows a schematic cross-sectional view of the bioreactor disposed on a frame according to another embodiment of the invention.
Figure 9:
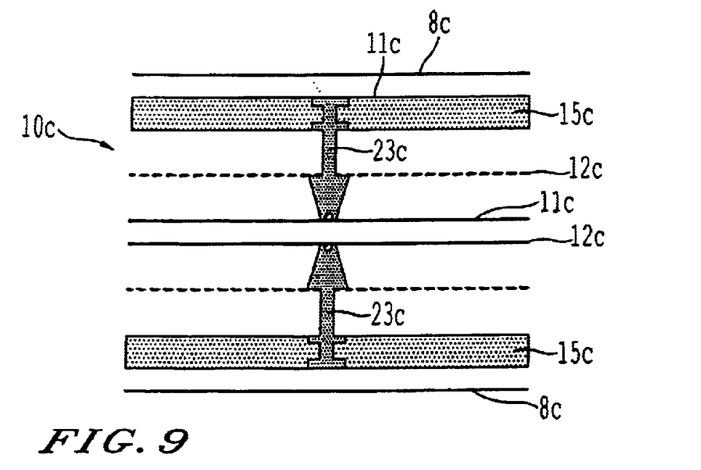
FIG. 9 shows a longitudinal cross-sectional view of the bioreactor of FIG. 8.
Figure 10:
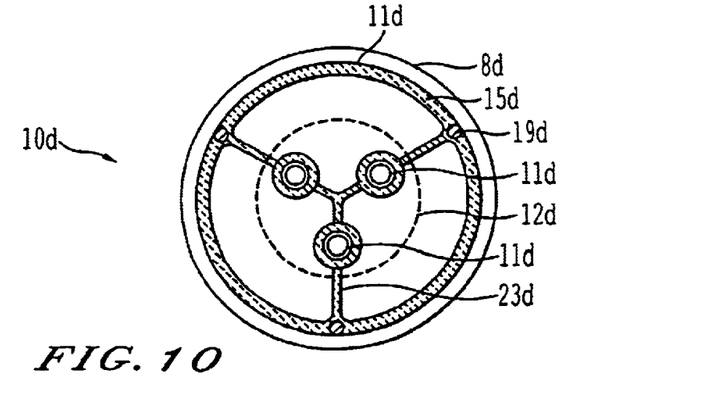
FIG. 10 shows a cross-sectional view of the bioreactor according to another embodiment of the invention.
Figure 11:
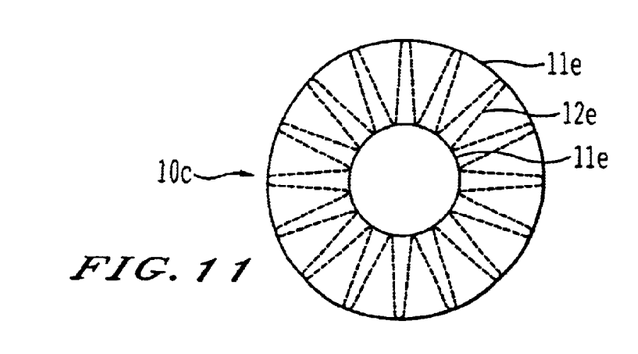
FIG. 11 shows a cross-sectional view of the bioreactor according to another embodiment of the invention.
Figure 12:
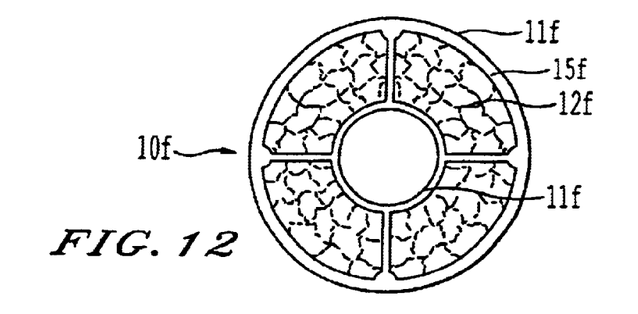
FIG. 12 shows a cross-sectional view of the bioreactor according to another embodiment of the invention.
Figure 13:
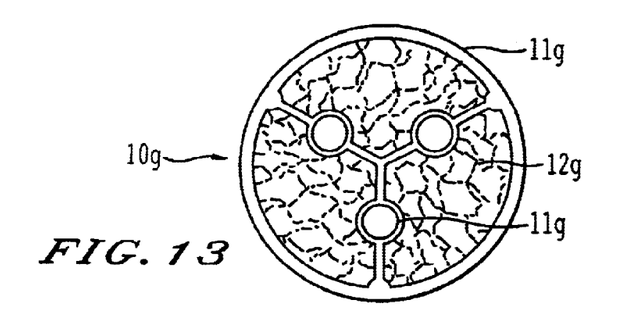
FIG. 13 shows a cross-sectional view of the bioreactor according to another embodiment of the invention.
Figure 14:
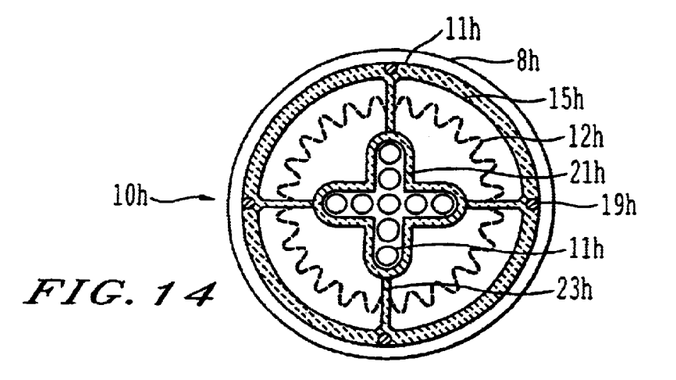
FIG. 14 shows a cross-sectional view of the bioreactor according to another embodiment of the invention.

To inoculate the bioreactor 10 it is at first filled via a feed line 19 from a container 30 with nutrient medium, which flows radially into the hollow space of the reactor. The corresponding feed line 19 is at first closed by a stop valve 31, while a discharge line 22 remains open. The feed lines 21 provided for the inoculation are opened by means of their feed stop valves 32 and the parent cells, which were taken from a patient before the radiotherapy or chemotherapy, can be injected through these reed lines into the reactor module 10 for example by means of a syringe. After this process the feed lines 21 provided for the inoculation and the discharge line 22 are closed. The parent cells are located in the receiving device and can settle the latter.

After a certain time that is advantageous to an even distribution and settlement of the parent cells the feed line 19 and one discharge line 22 are opened to promote cell growth. Tempered nutrient solution is then fed through the feed line 19. In the course of the cultivation process the amount of nutrient solution fed per unit of time can be gradually increased, as there are more cells present with an increasing duration of the cultivation process so that the nutrient demand grows.

The feeding and discharge of the nutrient medium is effected in such a way that the hollow space of the bioreactor 10, which is circular in cross section, and consequently the receiving device is flowed through as uniformly as possible. Through this a same and constant nutrient gradient is ensured over the entire surface of the cell carrier. At the same time detrimental metabolic products are removed from the bioreactor 10 by the nutrient flow in a quick and reliable manner.

After the exit of the nutrient medium via the discharge line 22 the nutrient medium passes through a first measuring device 33, with which the content of nutrients and harmful substances as well as further physical and chemical values of state are determined. The determined values serve to control and monitor the cultivation process by means of an appropriate control device. This can furthermore be connected to a second measuring device 34 located in the feed line 19. After a cleaning and reprocessing carried out in a reprocessing unit 35 located in the circle the nutrient medium can be re-fed into the container 30, with a pump 36 being provided as flow generating device.

Finally, for the removal of cultivated cells enzymes are fad via the line 21, which cause a detachment of the parent cells from the carrier element 12. For this the discharge line 22 is closed through a stop valve 37 and a physiological solution is being fed. The parent cells can now be sucked off by means of a syringe through the line 21 provided for the inoculation. The parent cells produced thereby can now be washed and, if required, be submitted to further treatment steps before being used for a further application, e.g. as blood substitute or implant. For the ventilation a vent valve 38 is arranged at the module housing of the bioreactor 10,

What is claimed is:

1. Bioreactor comprising:

a cell comprising:

first, second, and third carrier plates having predetermined thicknesses disposed between top and bottom covers;

two partition wall elements having membranes configured to be permeable to a nutrient medium and substantially impermeable to an organic material cultivated in the cell, the two partition wall elements disposed in the first and third carrier plates; and a carrier element configured to be permeable to the nutrient medium and to permit adhesion of the organic material thereto, the carrier element disposed in the second carrier plate between the first and third carrier plates.

2. Bioreactor according to claim 1, wherein the carrier element comprises a three-dimensional structure.

3. Bioreactor according to claim 1, wherein the carrier element comprises a textile carrier material.

4. Bioreactor according to claim 3, wherein the textile carrier material is surface-treated, and a bio-compatible surface is formed with a structure adapted for an adhesion of the organic material.

5. Bioreactor according to claim 1, wherein at least one of the two partition wall elements and the carrier element is disposed in a circular void defined in the carrier plates.

6. Bioreactor according to claim 1, wherein a plurality of cells are arranged in at least one of parallel and serial.

7. Bioreactor according to claim 1, further comprising:

a control device configured to control at least one of a flow generating device, a temperature adjusting unit, a gasing unit, and a degasing unit.

8. Bioreactor according to claim 7, further comprising:

a sensor device connected to the control device and configured to determine at least one of a physical and a chemical property of the nutrient medium.

9. Bioreactor according to claim 1, further comprising:

means for feeding and discharging the nutrient medium to the cell; and means for introducing and removing the organic material from the cell.

10. Method for cultivating the organic material, comprising:

introducing the organic material to the carrier element of the bioreactor of claim 1; and passing the nutrient medium between the two partition wall elements to the carrier element.

11. Method according to claim 10, further comprising:

sterilizing the carrier element prior to introducing the organic material to the carrier element.

12. Method according to claim 10, further comprising:

introducing an enzyme adapted to detach the adhered organic material from the carrier element.

13. Method according to claim 10, further comprising:

changing a direction of flow of the nutrient medium through the carrier element during detachment of the organic material from the carrier element.

14. Method according to claims 10, further comprising:

changing one of a chemical and physical property, a stoichiometrical composition, a temperature, a pressure, and a rate of flow of the nutrient medium during detachment of the organic material from the carrier element.

15. Method according to claim 10, further comprising:

measuring at least one of a chemical and a physical property of the nutrient medium;

analyzing the measured property; and controlling detachment of the organic material from the carrier element based on the analyzed property.

16. Method according to claim 10, further comprising:

passing the nutrient medium through multiple cells arranged in at least one of parallel and serial.

* * * * *

UNITED STATES PATENT AND TRADEMARK OFFICE
CERTIFICATE OF CORRECTION

PATENT NO. : 6,844,187 B1
DATED : January 18, 2005
INVENTOR(S) : Wechsler et al.

It is certified that error appears in the above-identified patent and that said Letters Patent is hereby corrected as shown below:

Title page,
Items [75] and [30], Inventors, city of residence and Foreign Application Priority Data, should read:
-- [75] Inventors: Thomas Wechsler, Zuerich (CH); Ulrich Baer, Heiden (CH); Christian Oehr, Herrenberg (DE); Thomas Graeve, Stuttgart (DE)

[30] Foreign Application Priority Data
Jul. 12, 1999  (DE) ............................ 199 32 439 --

Signed and Sealed this

Twenty-fourth Day of May, 2005

JON W. DUDAS
*Director of the United States Patent and Trademark Office*